United States Patent
Fukushima et al.

(10) Patent No.: US 9,862,660 B2
(45) Date of Patent: Jan. 9, 2018

(54) METHOD FOR PURIFYING FLUID THAT INCLUDES TRIFLUOROETHYLENE, AND METHOD FOR PRODUCING TRIFLUOROETHYLENE

(71) Applicant: ASAHI GLASS COMPANY, LIMITED, Chiyoda-ku (JP)

(72) Inventors: Masato Fukushima, Chiyoda-ku (JP); Satoshi Kawaguchi, Chiyoda-ku (JP); Maki Shigematsu, Chiyoda-ku (JP); Yoshinobu Kadowaki, Chiyoda-ku (JP); Yukio Tanaami, Chiyoda-ku (JP)

(73) Assignee: Asahi Glass Company, Limited, Chiyoda-ku (JP)

(*) Notice: Subject to any disclaimer, the term of this patent is extended or adjusted under 35 U.S.C. 154(b) by 0 days.

(21) Appl. No.: 15/234,409

(22) Filed: Aug. 11, 2016

(65) Prior Publication Data

US 2016/0347693 A1    Dec. 1, 2016

Related U.S. Application Data

(63) Continuation of application No. PCT/JP2015/054643, filed on Feb. 19, 2015.

(30) Foreign Application Priority Data

Feb. 20, 2014 (JP) ................... 2014-030854
Apr. 28, 2014 (JP) ................... 2014-092296

(51) Int. Cl.
  C07C 17/389    (2006.01)
  C07C 17/23     (2006.01)
  C07C 17/354    (2006.01)
  C07C 17/269    (2006.01)
  C07C 17/25     (2006.01)
  C07C 17/37     (2006.01)

(52) U.S. Cl.
  CPC .............. C07C 17/23 (2013.01); C07C 17/25 (2013.01); C07C 17/269 (2013.01); C07C 17/354 (2013.01); C07C 17/37 (2013.01); C07C 17/389 (2013.01)

(58) Field of Classification Search
  CPC .................................................. C07C 17/389
  See application file for complete search history.

(56) References Cited

U.S. PATENT DOCUMENTS

| | | | |
|---|---|---|---|
| 2,456,255 A | * | 12/1948 | Coffman ............... C08F 14/185 526/229 |
| 3,215,747 A | | 11/1965 | Fainberg et al. |
| 6,274,782 B1 | | 8/2001 | Ohno et al. |
| 2010/0191024 A1 | | 7/2010 | Uenveren et al. |
| 2013/0131402 A1 | | 5/2013 | Millefanti et al. |
| 2015/0094432 A1 | | 4/2015 | Leduc et al. |

FOREIGN PATENT DOCUMENTS

| | | |
|---|---|---|
| FR | 2 987 358 A1 | 8/2013 |
| JP | 40-2132 | 2/1965 |
| JP | 2009-539598 | 11/2009 |
| JP | 2010-533151 | 10/2010 |
| JP | 2013-534529 | 9/2013 |
| JP | 2013-241389 | 12/2013 |
| JP | 2013-241390 | 12/2013 |
| WO | WO 2013/151070 A1 | 10/2013 |

OTHER PUBLICATIONS

Furuta I (Furuta, S. et al. Publication No. WO2013151070A1, Published Oct. 10, 2013; pp. 1-8 English translation).*
Furuta II (Furuta, S. et al. Patent No. JP2013241389A, Published Dec. 5, 2013; pp. 1-10; English translation).*
International Search Report dated May 12, 2015 in PCT/JP2015/054643 filed on Feb. 19, 2015.
Bao-Chuan Meng et al. "Selective Liquid-phase Hydrodechlorination of Chlorotrifluoroethylene over Palladium-Supported Catalysts: Activity and Deactivation," Catalysis Letters, vol. 138, Nos. 1-2, Aug. 2010, 9 Pages.

* cited by examiner

Primary Examiner — Medhanit W Bahta
(74) Attorney, Agent, or Firm — Oblon, McClelland, Maier & Neustadt, L.L.P.

(57) ABSTRACT

To provide a method for purifying trifluoroethylene, by which from a fluid containing trifluoroethylene, a $C_{1-5}$ alkane or alkene (excluding trifluoroethylene) in which at least one hydrogen atom may be substituted with a chlorine atom or a fluorine atom can be efficiently removed, and a method for producing trifluoroethylene by which trifluoroethylene can be efficiently produced.
A fluid containing trifluoroethylene is brought into contact with at least one type of synthetic zeolite selected from synthetic zeolites 3A, 4A and 5A.

10 Claims, No Drawings

METHOD FOR PURIFYING FLUID THAT INCLUDES TRIFLUOROETHYLENE, AND METHOD FOR PRODUCING TRIFLUOROETHYLENE

TECHNICAL FIELD

The present invention relates to a method for purifying a fluid containing trifluoroethylene and a $C_{1-5}$ alkane or alkene in which at least one hydrogen atom may be substituted with a chlorine atom or a fluorine atom, and a method for producing trifluoroethylene.

BACKGROUND ART

Heretofore, as a working fluid such as a refrigerant for a refrigerator, a refrigerant for an air-conditioning apparatus, a working fluid for power generation system (such as exhaust heat recovery power generation), a working fluid for a latent heat transport apparatus (such as a heat pipe) or a secondary cooling fluid, a hydrofluorocarbon (HFC) such as difluoromethane (HFC-32), tetrafluoroethane or pentafluoroethane (HFC-125), which has less influence over the ozone layer, has been used. Further, by new environmental regulation, a new refrigerant to be used for a refrigerator, an air-conditioning apparatus, a heat pump apparatus, etc. is required, and compounds having low global warming potential (GWP) attract attention. In this specification, abbreviated names of halogenated hydrocarbon compounds are described in brackets after the compound names, and in this specification, the abbreviated names are employed instead of the compound names as the case requires. Further, (E), (Z) or the like before the compound names or after the abbreviated names of compounds represent E-form or Z-form of geometric isomers.

As such a working fluid, a hydrofluoroolefin (HFO) having a carbon-carbon double bond is proposed, which has less influence over the ozone layer and which has less influence over global warming, since the carbon-carbon double bond is likely to be decomposed by OH radicals in the air.

Particularly, as the HFO, trifluoroethylene (HFO-1123) is considered as promising as an alternative to a saturated hydrofluorocarbon (HFC) refrigerant having a high GWP.

When a HFO is used as a refrigerant, if the HFO contains a large quantity of water (moisture), various problems in the reliability and in the performance may arise. In order to suppress such unfavorable influences, the water content is preferably as low as possible.

As a method for drying the HFO, Patent Document 1 discloses a method of bringing a gas containing a fluoropropene into contact with a molecular sieve having a maximum opening of from about 3 Å to about 5 Å. It discloses as the molecular sieve zeolites 3A, 4A and 5A, and discloses an example of drying (desiccating) a fluid containing 2,3,3,3-tetrafluoropropene (HFO-1234yf) using such a molecular sieve. Further, Patent Document 2 discloses a method for removing water in a fluid containing a fluoroolefin and a $C_1$ alkane by bringing the fluid into contact with synthetic zeolite 3A.

However, a method for drying a fluid containing HFO-1123 is not disclosed in Patent Documents 1 and 2. Particularly in a case where the fluid contains HFO-1123 and a $C_{1-5}$ alkane or alkene in which at least one hydrogen atom may be substituted with a chlorine atom or a fluorine atom, it is found that by the method disclosed in Patent Document 1, the $C_{1-5}$ alkane or alkene is adsorbed in the molecular sieve and removed in some cases, and it is not possible to remove only water in the fluid.

Further, in a method for producing HFO-1123, HFO-1123 is obtained as a compound contained in a fluid containing a $C_{1-5}$ alkane or alkene in which at least one hydrogen atom may be substituted with a chlorine atom or a fluorine atom, and it is difficult to obtain high purity HFO-1123 from the fluid with a sufficiently high yield. For example, in a case where HFO-1123 is to be obtained by subjecting chlorotrifluoroethylene (CTFE) to hydrogen reduction in the presence of a palladium or platinum catalyst, hydrogen reduction excessively proceeds since a transition metal catalyst is used, and together with the desired HFO-1123, excessively reduced (E)-1,2-difluoroethylene (HFO-1132(E)) forms as a by-product. It is difficult to purify and separate HFO-1123 since HFO-1132(E) has a boiling point close to that of the desired HFO-1123, and high purity HFO-1123 cannot be obtained with a sufficiently high yield.

PRIOR ART DOCUMENTS

Patent Documents

Patent Document 1: JP-A-2009-539598
Patent Document 2: JP-A-2013-241389

DISCLOSURE OF INVENTION

Technical Problem

Under these circumstances, the object of the present invention is to provide a method for purifying HFO-1123, by which from a fluid containing HFO-1123 and a $C_{1-5}$ alkane or alkene, impurities other than HFO-1123, such as the $C_{1-5}$ alkane or alkene or water, can be efficiency removed.

Further, another object of the present invention is to provide a method for producing HFO-1123, by which HFO-1123 can be efficiently produced by purifying a fluid containing HFO-1123 and a $C_{1-5}$ alkane or alkene.

Solution to Problem

The method for purifying trifluoroethylene of the present invention comprises bringing a fluid containing trifluoroethylene and a $C_{1-5}$ alkane or alkene (excluding trifluoroethylene) in which at least one hydrogen atom may be substituted with a chlorine atom or a fluorine atom, into contact with at least one type of synthetic zeolite selected from synthetic zeolites 3A, 4A and 5A to remove the $C_{1-5}$ alkane or alkene.

In the purification method of the present invention, the $C_{1-5}$ alkane or alkene is preferably at least one compound selected from the group consisting of chloromethane, fluoromethane, difluoromethane, chlorofluoromethane, trifluoromethane, chlorodifluoromethane, dichlorodifluoromethane, 1,1,2-trichloro-1,2,2-trifluoroethane, 1,2-dichloro-1,1,2-trifluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-1,1,2-trifluoroethane, 1,1,2,2-tetrafluoroethane, 1,1,1,2-tetrafluoroethane, 2-chloro-1,1-difluoroethane, 1-chloro-1,1-difluoroethane, 1,1,2-trifluoroethane, 1,1,1-trifluoroethane, 1,1-difluoroethane, 1,2-difluoroethane, 1,1,1,2,2,3,3-heptafluoropropane, 1,1,1,2,3,3,3-heptafluoropropane, 1,1,1,3,3,3-hexafluoropropane, 1,1,1,2,3,3-hexafluoropropane, E- and/or Z-1,2-difluoroethylene, 1,1-difluoroethylene, fluoroethylene, 3,3-difluoropropene, 3,3,3-trifluoropropene, 2,3,3,3- tetrafluoropropene, E- and/or Z-1,3,3,3-tetrafluoropropene, hexafluoropropene, chlorotrifluoroethylene, 1-chloro-2,2-difluoroethylene, E- and/or Z-1,2-dichlorofluoroethylene, E- and/or Z-1,2-dichloro-1,2-difluoroethylene, tetrafluoroethylene, E- and/or Z-1-chloro-2-fluoroethylene, perfluorocyclobutane, methane, ethane, ethylene, propane, propylene, n-butane, isobutane, 1-n-butene, 2-n-butene and isobutene.

In the purification method of the present invention, it is preferred that the $C_{1-5}$ alkane or alkene is (E)-1,2-difluoroethylene, and the synthetic zeolite is synthetic zeolite 4A and/or 5A. Further, it is preferred that the fluid further contains water, the synthetic zeolite is synthetic zeolite 3A, and water is removed by the contact.

Further, in the purification method of the present invention, the synthetic zeolite is preferably one preliminarily subjected to a heat treatment by a dry gas of from 100 to 400° C. or one preliminarily subjected to a heat treatment under reduced pressure.

The method for producing trifluoroethylene of the present invention comprises a purification step of bringing a fluid containing trifluoroethylene and a $C_{1-5}$ alkane or alkene (excluding trifluoroethylene) in which at least one hydrogen atom may be substituted with a chlorine atom or a fluorine atom, into contact with at least one type of synthetic zeolite selected from synthetic zeolites 3A, 4A and 5A to purify the fluid.

The production method of the present invention preferably comprises a production step of reducing chlorotrifluoroethylene with hydrogen gas in the presence of a catalyst to produce a fluid containing trifluoroethylene and a $C_{1-5}$ alkane or alkene (excluding trifluoroethylene) in which at least one hydrogen atom may be substituted with a chlorine atom or a fluorine atom, and the above preparation step.

The production method of the present invention preferably comprises a production step of subjecting a composition containing (chlorodifluoromethane and/or tetrafluoroethylene) and chlorofluoromethane to a synthetic reaction involving heat decomposition in the presence of a heating fluid to produce a fluid containing trifluoroethylene and a $C_{1-5}$ alkane or alkene (excluding trifluoroethylene) in which at least one hydrogen atom may be substituted with a chlorine atom or a fluorine atom, and the above purification step.

The production method of the present invention preferably comprises a production step of subjecting 1,1,1,2-tetrafluoroethane to dehydrofluorination in the presence of an alkali metal and/or an alkaline earth metal to produce a fluid containing trifluoroethylene and a 01-5 alkane or alkene (excluding trifluoroethylene) in which at least one hydrogen atom may be substituted with a chlorine atom or a fluorine atom, and the above purification step.

Further, in the production method of the present invention, the synthetic zeolite is preferably one preliminarily subjected to a heat treatment by a dry gas of from 100 to 400° C. or one preliminarily subjected to a heat treatment under reduced pressure.

In this specification, "a $C_{1-5}$ alkane or alkene (excluding trifluoroethylene) in which at least one hydrogen atom may be substituted with a chlorine atom or a fluorine atom" may sometimes be referred to simply as "$C_{1-5}$ alkane or alkene".

Advantageous Effects of Invention

According to the purification method of the present invention, from a fluid containing HFO-1123 and a $C_{1-5}$ alkane or alkene, impurities other than HFO-1123, such as the $C_{1-5}$ alkane or alkene and water, can be efficiently removed.

Further, according to the production method of the present invention, HFO-1123 can be efficiently produced by purifying a fluid containing HFO-1123 and a $C_{1-5}$ alkane or alkene.

DESCRIPTION OF EMBODIMENTS

Now, embodiments of the present invention will be described.
<Method for Purifying Fluid Containing HFO-1123>

The method for purifying a fluid containing HFO-1123 according to a first embodiment of the present invention is a method for purifying a fluid containing HFO-1123 by bringing a fluid containing HFO-1123 and a $C_{1-5}$ alkane or alkene in which at least one hydrogen atom may be substituted with a chlorine atom or a fluorine atom into contact with a specific synthetic zeolite to remove the $C_{1-5}$ alkane or alkene. HFO-1123 is hardly adsorbed on any of the synthetic zeolites 3A, 4A and 5A. Accordingly, by bringing the fluid in the present invention into contact with at least one type of synthetic zeolite selected from synthetic zeolites 3A, 4A and 5A, the $C_{1-5}$ alkane or alkene is removed and the fluid is purified.

($C_{1-5}$ Alkane or Alkene)

The $C_{1-5}$ alkane or alkene in the present invention is a $C_{1-5}$ alkane or alkene other than HFO-1123, in which at least one hydrogen atom may be substituted with a chlorine atom and/or a fluorine atom. Such a $C_{1-5}$ alkane or alkene is adsorbed on the synthetic zeolite 4A or 5A. The $C_{1-5}$ alkane or alkene may be any of linear, cyclic and branched.

Further, in the $C_{1-5}$ alkane or alkene, the hydrogen atom may be substituted only with a chlorine atom, only with a fluorine atom, or with both a chlorine atom and a fluorine atom. The total number of chlorine atoms and fluorine atoms in one molecule of the $C_{1-5}$ alkane or alkene is preferably at least the number of hydrogen atoms in the $C_{1-5}$ alkane or alkene, in view of low flammability. The number of chlorine atoms is preferably from 0 to 4, more preferably from 1 to 3. When the number of chlorine atoms is at least 5, such an alkane or alkene tends to have a high boiling point, and when the fluid of the present invention is handled in a gaseous state, gas-liquid separation is likely to occur. The number of fluorine atoms is preferably from 2 to 12, more preferably from 3 to 11.

Particularly, the $C_{1-5}$ alkane or alkene is preferably one in which the total number of hydrogen atoms, chlorine atoms and fluorine atoms in one molecule is from 4 to 8, more preferably from 4 to 6.

Specifically, the $C_{1-5}$ alkane or alkene may, for example, be chloromethane (HCC-40), fluoromethane (HFC-41), difluoromethane (HFC-32), chlorofluoromethane (HCFC-31), trifluoromethane (HFC-23), chlorodifluoromethane (HCFC-22), dichlorodifluoromethane (CFC-12), 1,1,2-trichloro-1,2,2-trifluoroethane (CFC-113), 1,2-dichloro-1,1,2-trifluoroethane (HCFC-123a), 1-chloro-1,2,2,2-tetrafluoroethane (HCFC-124), 1-chloro-1,1,2,2-tetrafluoroethane (HCFC-124a), pentafluoroethane (HFC-125), 1-chloro-1,2,2-trifluoroethane (HCFC-133), 1-chloro-1,1,2-trifluoroethane (HCFC-133b), 1,1,2,2-tetrafluoroethane (HFC-134), 1,1,1,2-tetrafluoroethane (HFC-134a), 2-chloro-1,1-difluoroethane (HCFC-142), 1-chloro-1,1-difluoroethane (HCFC-142b), 1,1,2-trifluoroethane (HFC-143), 1,1,1-trifluoroethane (HFC-143a), 1,1-difluoroethane (HFC-152a), 1,2-difluoroethane (HFC-152), 1,1,1,2,2,3,3-heptafluoropropane (HFC-227ca), 1,1,1,2,3,3,3-heptafluoropropane (HFC-227ea), 1,1,1,3,3,3-hexafluoropropane (HFC-236fa), 1,1,1,2,3,3- hexafluoropropane (HFC-236ea), E- and/or Z-1,2-difluoro-ethylene (HFO-1132), 1,1-difluoroethylene (HFO-1132a), fluoroethylene (HFO-1141), 3,3-difluoropropene (HFO-1252zf), 3,3,3-trifluoropropene (HFO-1243zf), 2,3,3,3-tetrafluoropropene (HFO-1234yf), E- and/or Z-1,3,3,3-tetrafluoropropene (HFO-1234ze) hexafluoropropene (FO-1216), chlorotrifluoroethylene (CFO-1113), 1-chloro-2,2-difluoroethylene (HCFO-1122), E- and/or Z-1,2-dichlorofluoroethylene (HCFO-1122a), E- and/or Z-1,2-dichloro-1,2-difluoroethylene (CFO-1112), tetrafluoroethylene (FO-1114), E- and/or Z-1-chloro-2-fluoroethylene (HCFO-1131), perfluorocyclobutane (RC-318), methane, ethane, ethylene, propane, propylene, n-butane, isobutane, 1-n-butene, 2-n-butene or isobutene. The fluid according to this embodiment preferably contains at least one of such compounds. Here, "E- and/or Z-" means a mixture of E-form and Z-form.

The $C_{1-5}$ alkane or alkene is preferably a compound contained in a reaction product obtained by the after-described (I) hydrogen reduction of CFO-1113. Such a compound may be CFO-1113, HFO-1132, HFO-1132a, HCFO-1122, HCFO-1122a, HFC-143, methane, HFC-152a, HFC-152, HCFC-142, HCFC-142b, HCFC-133, HCFC-133b, HCFC-123a, CFC-113 or CFO-1112.

Further, the $C_{1-5}$ alkane or alkene is preferably a compound contained in a reaction product obtained by the after-described (II) synthetic reaction involving heat decomposition of (HCFC-22 and/or FO-1114) and HCFC-31. Such a compound may be HCFC-22, HCFC-31, HFO-1132, HFO-1132a, HFO-1141, CFO-1113, HCFO-1122, HCFO-1122a, HFC-143, FO-1114, HCFO-1131, HFO-1252zf, HFO-1243zf, HFO-1234yf, HFO-1234ze, FO-1216, HFC-125, HFC-134, HFC-134a, HFC-143a, HCFC-124, HCFC-124a, HFC-227ca, HFC-227ea, HFC-236fa, HFC-236ea, CFC-12, HFC-23, HFC-32, HFC-41, HCC-40, RC-318 or methane.

Further, the $C_{1-5}$ alkane or alkene is preferably a compound contained in a reaction product obtained by the after-described (III) dehydrofluorination of HFC-134a. Such a compound may be HFC-134a, HFO-1132, HFO-1132a, HFC-143, methane, ethane, ethylene, propane, propylene, n-butane, isobutane, 1-n-butene, 2-n-butene, isobutene, HFO-1141, HFO-1252zf, HFO-1243zf, HFO-1234yf, HFO-1234ze, FO-1216, HFC-125, HFC-134, HFC-143a, HFC-227ca, HFC-227ea, HFC-236fa, HFC-236ea, HFC-32, HFC-23 or HFC-41.

Particularly, the $C_{1-5}$ alkane or alkene is preferably HFO-1132(E), which can be efficiently removed by contact with the synthetic zeolite.

(Fluid Containing HFO-1123 and $C_{1-5}$ Alkane or Alkene)

The fluid in the present invention is not particularly limited so long as it is a fluid containing HFO-1123 and the $C_{1-5}$ alkane or alkene. The fluid to be purified may be either a liquid or a gas. Further, the fluid may further contain water. The water contained in the fluid may be water formed in the HFO-1123 production process, water included when the reaction product obtained in the HFO-1123 production process is washed with water or an alkali, or the like. In a case where the fluid further contains water, the content of water in the fluid is preferably at most 1 mass %, more preferably at most 0.5 mass %, most preferably at most 0.1 mass %. The fluid should contain HFO-1123 even in a very small amount, and the content of HFO-1123 is preferably at least 5 mass %, more preferably at least 10 mass %.

In the fluid in the present invention, the content ratio of HFO-1123 and the $C_{1-5}$ alkane or alkene is not particularly limited, however, in view of the subsequent removal efficiency, the molar amount of HFO-1123 contained is preferably larger than the total molar amount of the $C_{1-5}$ alkane or alkene contained, and the molar ratio represented by ($C_{1-5}$ alkane or alkene)/(HFO-1123) is more preferably from 0.1 to 0.7.

As the fluid in the present invention, for example, a reaction product containing HFO-1123 obtained by reacting various material components for the purpose of producing HFO-1123 may be used. That is, as shown in the following, in a case where a reaction product contains HFO-1123 in the HFO-1123 production process, a gas of the reaction product is used as it is as a starting fluid, and impurities other than HFO-1123, such as HFO-1132(E) and water in the fluid (hereinafter sometimes referred to simply as "impurities other than HFO-1123") are removed, and by means of the subsequent purification step, high purity HFO-1123 can be obtained. Further, also in a case where a gas of the reaction product is washed with water or an alkali to remove an acidic substance such as hydrogen fluoride or hydrogen chloride contained in the reaction product, and the obtained gas mixture is used as a starting fluid, likewise, impurities other than HFO-1123 in the fluid are removed, whereby high purity HFO-1123 can be obtained.

As a fluid to be purified by the purification method of the present invention, specifically, a reaction product containing HFO-1123 obtained by any of the following processes (I) to (III) may be mentioned.

(I) CFO-1113 and hydrogen gas are reduced in the presence of a catalyst.

(II) A composition containing (HCFC-22 and/or FO-1114) and HCFC-31 is subjected to a synthetic reaction involving heat decomposition in the presence of a heating fluid.

(III) HFO-134a is subjected to dehydrofluorination in the presence of an alkali metal and/or an alkaline earth metal.

(Synthetic Zeolite)

The synthetic zeolite in the present invention is a synthetic zeolite having a chemical composition represented by the following formula (1):

$$K_xNa_y[(AlO_2)_{12}(SiO_2)_{12}] \cdot 27H_2O \quad (1)$$

wherein x+y=12, and x:y=4:6 to 8:2.

The synthetic zeolites 3A, 4A and 5A in the present invention are synthetic zeolites having a pore size of from 0.25 to 0.45 nm.

The synthetic zeolite 3A in the present invention is a synthetic zeolite having a pore size of 0.28±0.03 nm. However, due to expansion and kinetic energy of molecules which enter the cavity at a usual operation temperature, molecules having an effective diameter up to 0.3 nm can pass through the synthetic zeolite 3A.

The synthetic zeolite 4A in the present invention is a synthetic zeolite having a pore size of 0.35±0.03 nm.

The synthetic zeolite 5A in the present invention is a synthetic zeolite having a pore size of 0.42±0.03 nm.

As such a synthetic zeolite, type A synthetic zeolites 3A, 4A and 5A may be mentioned. As commercially available products, Molecular Sieves 3A, 4A and 5A (tradename, manufactured by UNION SHOWA K.K.) may, for example, be mentioned. The pore sizes of the molecular sieves may be measured by a constant volume gas adsorption method. As an adsorption gas used for the constant volume gas adsorption method, $N_2$, $CO_2$, $CH_4$, $H_2$, Ar or the like may be mentioned.

The synthetic zeolite in the present invention is preferably preliminarily subjected to a heat treatment by a dry gas of from 100 to 400° C. or a heat treatment under reduced pressure, before used for purification of the fluid containing HFO-1123. By such a treatment, the zeolite is activated, and the efficiency to remove impurities other than HFO-1123 will improve.

(Removal of HFO-1132(E) from Fluid Containing HFO-1123)

In a case where the fluid in the present invention contains HFO-1132(E), HFO-1132(E) is likely to be adsorbed on any of the synthetic zeolites 3A, 4A and 5A. Accordingly, by using as the synthetic zeolite at least one type selected from the synthetic zeolites 3A, 4A and 5A, HFO-1132(E) can be efficiently removed from the fluid in the present invention, whereby the fluid can be purified.

(Removal of Water from Fluid Containing HFO-1123)

In a case where the fluid in the present invention further contains water, water is likely to be adsorbed on synthetic zeolite 3A. Accordingly, in the purification method of the present invention, by bringing the fluid containing HFO-1123 and a $C_{1-5}$ alkane or alkene in which at least one hydrogen atom may be substituted with a chlorine atom or a fluorine atom into contact with synthetic zeolite 3A, water in the fluid is selectively removed, and the fluid can be purified.

(Method of Bringing Synthetic Zeolite and Fluid into Contact with Each Other)

In the present invention, by bringing the fluid containing HFO-1123 and a $C_{1-5}$ alkane or alkene into contact with the above synthetic zeolite, impurities other than HFO-1123, such as the $C_{1-5}$ alkane or alkene and water, in the fluid are adsorbed and removed.

In the present invention, the synthetic zeolites 3A, 4A and 5A may be used alone or in combination of two or more. Further, in addition to the synthetic zeolite 3A, 4A or 5A, synthetic zeolite 13X which is a type X synthetic zeolite may be used in combination. In general, each of the synthetic zeolites 3A, 4A and 5A can adsorb the $C_{1-5}$ alkane or alkene or water, however, compounds which are easily adsorbed vary depending upon the composition of the fluid to be purified or the type (the degree of the pore size) of the synthetic zeolite. In the present invention in which the fluid containing HFO-1123 and a $C_{1-5}$ alkane or alkene is to be purified, synthetic zeolite 4A is likely to adsorb, for example, a $C_1$ alkane in the fluid in the present invention. Further, synthetic zeolite 5A is likely to adsorb, for example, a $C_{1-2}$ alkane or alkene. From such a viewpoint, by using synthetic zeolite 3A, 4A or 5A by itself or in combination, among impurities other than HFO-1123 contained in the fluid, desired compounds can be removed to a desired extent.

In the purification method of the present invention, in a case where two or more types of synthetic zeolites 3A, 4A and 5A are used in combination, the order of contact of synthetic zeolites 3A, 4A and 5A is not particularly limited. The fluid may be brought into contact with two or more types of synthetic zeolites 3A, 4A and 5A in order, or may be brought into contact with two or more types selected from synthetic zeolites 3A, 4A and 5A simultaneously e.g. by mixing the zeolites. In a case where the fluid is brought into contact with the zeolites in order, the fluid is brought into contact with each of the synthetic zeolites by the aftermentioned method for bringing the fluid and the synthetic zeolite into contact with each other.

The fluid to be brought into contact with the synthetic zeolite may be either a gas or a liquid. When the fluid in a liquid state is brought into contact with the synthetic zeolite, the fluid is liquefied at low temperature or under high pressure, or may be dissolved in a solvent to be in a liquid state. By using as such a solvent a solvent having a boiling point higher than that of HFO-1123, the solvent can easily be removed from the fluid after purification e.g. by distillation.

Now, a method of using a gaseous mixture as the fluid will be described. In this method, for example, it is preferred to form an adsorption layer packed with the synthetic zeolite and to make a gas mixture containing HFO-1123 to flow through the adsorption layer. The contact by such a method may be conducted by the batch or continuously.

The packing density of the synthetic zeolite in the adsorption layer is preferably at least 0.1 g/cm$^3$, more preferably at least 0.25 g/cm$^3$. When the packing density of the synthetic zeolite is at least the lower limit value, the packing amount of the synthetic zeolite per unit volume tends to be large, and the amount of the gas mixture treated can be increased, whereby the efficiency to remove impurities other than HFO-1123 will improve. There may be one adsorption layer or two or more adsorption layers. In a case where there are two or more adsorption layers, such adsorption layers may be connected either in parallel or in series.

The temperature of the adsorption layer at the time of the contact is preferably from −10 to 70° C., more preferably from −10 to 30° C. When the temperature of the adsorption layer is at least the lower limit value, the efficiency of the synthetic zeolite to remove impurities other than HFO-1123 will improve. When the temperature of the adsorption layer is at most the upper limit value, the energy required for cooling tends to be smaller, and simple equipment is enough.

The pressure (gauge pressure) of the gas mixture at the time of the contact is preferably from 10 to 2,000 kPa, more preferably from 100 to 1,000 kPa. When the pressure is at least the lower limit value, the efficiency to remove impurities other than HFO-1123 will improve. When the pressure is at most the upper limit value, such is preferred in view of handling efficiency, and simple equipment is enough.

The contact time of the adsorption layer and the gas mixture which is made to flow through the adsorption layer is preferably from 1 to 1,000 seconds, more preferably from 3 to 300 seconds. When the contact time of the adsorption layer and the gas mixture is at least the lower limit value, the efficiency to remove impurities other than HFO-1123 will improve. When the contact time of the adsorption layer and the gas mixture is at most the upper limit value, the adsorption layer used for purification of the fluid is small, and thus simple equipment is enough.

Further, in view of the removal efficiency, the total amount of impurities other than HFO-1123 contained in the gas mixture which is made to flow through the adsorption layer is preferably at most 0.5 mass %, most preferably at most 0.2 mass % based on the total amount of the synthetic zeolite in the adsorption layer. That is, in the method of using as the fluid a gaseous mixture, the amount of the mixture to be brought into contact with the synthetic zeolite is preferably adjusted so that the proportion of the impurities other than HFO-1123 to the synthetic zeolite is at most the upper limit value.

As a reactor to be used for the contact of the gas mixture and the synthetic zeolite, a known reactor which can be packed with synthetic zeolite to form the adsorption layer may be mentioned. As the material of the reactor, for example, glass, iron, nickel, or an alloy containing iron or nickel as the main component, or a fluororesin such as a tetrafluoroethylene/perfluoro(alkyl vinyl ether) copolymer (PFA) may be mentioned.

Now, a method of using as the fluid a liquid mixture will be described. In this method, an adsorption layer is formed in the same manner as the method of using as the fluid a gaseous mixture, and a liquid mixture containing HFO-1123 is made to flow through the adsorption layer. Otherwise, in a reactor packed with the synthetic zeolite, the synthetic zeolite and the fluid are mixed and as the case requires, stirred. In the method of mixing the synthetic zeolite and a liquid mixture containing HFO-1123 in a reactor, after purification of the liquid mixture containing HFO-1123, the purified liquid mixture and the synthetic zeolite may be separated by precipitation or filtration. The contact in such a method may be conducted by the batch or continuously.

Preferred embodiments of the packing density of the synthetic zeolite in the adsorption layer and the constitution of the adsorption layer are the same as the method of using as the fluid a gaseous mixture.

The temperature of the adsorption layer at the time of the contact is preferably from −30 to 70° C., more preferably from −30 to 40° C. When the temperature of the adsorption layer is at least the lower limit value, the rate of removal of impurities other than HFO-1123 will improve. When the temperature of the adsorption layer is at most the upper limit value, the energy required for cooling tends to be smaller, and simple equipment is enough.

The pressure (gauge pressure) of the liquid mixture at the time of the contact is preferably from 100 to 2,000 kPa, more preferably from 100 to 1,000 kPa. When the pressure is at least the lower limit value, the rate of removal of impurities other than HFO-1123 will improve. When the pressure is at most the upper limit value, such is preferred in view of handling efficiency, and simple equipment is enough.

The contact time of the adsorption layer and the liquid mixture which is made to flow through the adsorption layer is preferably from 1 to 1,000 seconds, more preferably from 3 to 300 seconds. When the contact time of the adsorption layer and the liquid mixture is at least the lower limit value, the efficiency to remove impurities other than HFO-1123 will improve. When the contact time of the adsorption layer and the liquid mixture is at most the upper limit value, the adsorption layer used for purification of the fluid is small, and thus simple equipment is enough.

Further, with a view to improving the efficiency to remove impurities other than HFO-1123, the total amount of impurities other than HFO-1123 contained in the liquid mixture which is made to flow through the adsorption layer is preferably at most 0.5 mass %, most preferably at most 0.2 mass % based on the total amount of the synthetic zeolite. That is, in the method of using as the fluid a liquid mixture, the amount of the mixture to be brought into contact with the synthetic zeolite is preferably adjusted so that the proportion of the impurities other than HFO-1123 to the synthetic zeolite is at most the upper limit value.

As a reactor to be used for the contact of the liquid mixture and the synthetic zeolite forming the adsorption layer, a reactor which can be packed with synthetic zeolite to form the adsorption layer may be used. As the material of the reactor, for example, glass, iron, nickel, or an alloy containing iron or nickel as the main component, or a fluororesin such as a tetrafluoroethylene/perfluoro(alkyl vinyl ether) copolymer (PFA) may be mentioned. The reactor in which the liquid mixture and the synthetic zeolite are mixed and brought into contact with each other, may, for example, be a reactor in which the mixture in a liquid state can be brought into contact with the synthetic zeolite at a desired temperature under a desired pressure, such as an autoclave.

<Method for Producing HFO-1123>

The method for producing HFO-1123 according to a second embodiment of the present invention comprises the above purification step of purifying the fluid containing HFO-1123.

In the production method of the present invention, for example, purification shown as the above first embodiment is conducted on an outlet gas obtained by the HFO-1123 production process (I) to (III) or a gas mixture obtained after acidic substances and the like are removed from the outlet gas, whereby from a fluid containing HFO-1123 and a $C_{1-5}$ alkane or alkene, impurities other than HFO-1123 can be efficiently removed.

(I) Hydrogen Reduction of CFO-1113

A material composition containing CFO-1113 and hydrogen is reacted in a gaseous phase in a reactor having a catalyst layer packed with a catalyst-supporting carrier to form a gas containing HFO-1123.

The main reaction in the reactor in this embodiment is shown in the following formula (2):

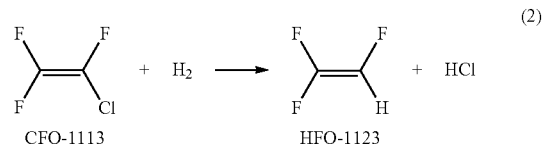 [SMILES: FC(F)=C(F)Cl ; "H2" ; FC=C(F)F ; Cl]

With respect to the ratio of CFO-1113 and hydrogen in the material composition, the proportion of hydrogen is preferably within a range of from 0.01 to 4.0 mol per 1 mol of CFO-1113. The contact time of CFO-1113 and the catalyst is preferably from 4 to 60 seconds, more preferably from 8 to 40 seconds.

The catalyst is preferably a palladium catalyst, more preferably a catalyst having only palladium or a palladium alloy supported on a carrier or a catalyst having palladium and a metal other than palladium supported on a carrier. The carrier may, for example, be activated carbon or a metal oxide (such as alumina, zirconia or silica).

In such hydrogen reduction of CFO-1113, a reaction product containing HFO-1123 and acidic substances such as hydrogen chloride is obtained as an outlet gas of the reactor. The acidic substances contained in the outlet gas are removed e.g. by washing with an alkali to obtain a gas mixture. Compounds other than HFO-1123 contained in the gas mixture may, for example, be CFO-1113 as the unreacted material, and HFO-1132, HFO-1132a, HCFO-1122, HCFO-1122a, HFC-143, methane, HFC-152a, HFC-152, HCFC-142, HCFC-142b, HCFC-133, HCFC-133b, HCFC-123a, CFC-113 and CFO-1112.

By conducting purification shown as the first embodiment on the outlet gas or the gas mixture thus obtained, from the fluid containing HFO-1123 and a $C_{1-5}$ alkane or alkene, impurities other than HFO-1123 can be efficiently removed. The above components other than HFO-1123 contained in the outlet gas or the gas mixture may be removed to a desired extent by a known means such as distillation. Further, the separated CFO-1113 may be recycled as a part of the material.

(II) Synthesis Involving Heat Decomposition of (HCFC-22 and/or FO-1114) and HCFC-31

A gas containing HFO-1123 is formed by a synthetic reaction involving heat decomposition using a material composition containing (HCFC-22 and/or FO-1114) and HCFC-31 in the presence of a heating fluid. In this production process, (HCFC-22 and/or FO-1114) and HCFC-31 in a molar ratio of 1:0.01 to 4.0 are supplied to a reactor as preliminarily mixed or separately and allowed to stay in the reactor for a predetermined time, and the heating fluid is supplied to the reactor. In the reactor, the material composition and the heating fluid are brought into contact with each other.

The main reaction in the reactor in this production process is shown in the following formula (3):

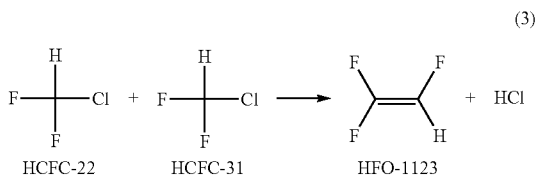

The material composition is subjected to heat decomposition and dehydrochlorination in the reactor to form a reaction mixture containing difluorocarbene (F$_2$C:) and HCFC-31, and the reaction mixture is considered to be converted to HFO-1123 by addition reaction directly or by means of one or more intermediates.

The material composition may contain, in addition to the two or three components, a fluorinated compound which may be heat-decomposed in the reactor to form F$_2$C:, for example, FO-1216, RC318, HFO-1132a, HFO-1113 or HFO-1123. When such a fluorinated compound which may be heat-decomposed in the reactor to form F$_2$C: is used for the material composition, a newly prepared fluorinated compound may be used, however, it is preferred to use a fluorinated compound formed as a by-product by the heat decomposition reaction of (HCFC-22 and/or FO-1114) and HCFC-31 according to this embodiment, from the viewpoint of recycle.

The material composition containing (HCFC-22 and/or FO-1114) and HCFC-31 may be introduced to the reactor at room temperature as it is, or its temperature when introduced to the reactor may be adjusted e.g. by heating so as to improve the reactivity in the reactor.

The heating fluid is a fluid which is not heat-decomposed at the temperature in the reactor and may be specifically one or more gases selected from water vapor, nitrogen and carbon dioxide. The heating fluid is preferably a gas containing water vapor in an amount of at least 50 vol % and containing nitrogen and/or carbon dioxide as the rest.

The amount of supply of the heating fluid is preferably from 20 to 98 vol % based on the total amount of the heating fluid and the material composition supplied. The contact time of the heating fluid and the material composition in the reactor is preferably from 0.01 to 10 seconds, and the pressure (gauge pressure) in the reactor is preferably from 0 to 2.0 MPa.

By such synthesis involving heat decomposition of (HCFC-22 and/or FO-1114) and HCFC-31, a reaction product containing HFO-1123 and acidic substances such as hydrogen chloride is obtained as an outlet gas of the reactor. The acidic substances contained in the outlet gas are removed e.g. by washing with an alkali to obtain a gas mixture. Compounds other than HFO-1123 contained in the gas mixture may, for example, be HCFC-22, FO-1114 and HCFC-31 as the unreacted materials, and HFO-1132, HFO-1132a, HFO-1141, CFO-1113, HCFO-1122, HCFO-1122a, HFC-143, HCFO-1131, HFO-1252zf, HFO-1243zf, HFO-1234yf, HFO-1234ze, FO-1216, HFC-125, HFC-134, HFC-134a, HFC-143a, HCFC-124, HCFC-124a, HFC-227ca, HFC-227ea, HFC-236fa, HFC-236ea, CFC-12, HFC-23, HFC-32, HFC-41, chloromethane, RC-318 and methane.

By conducting purification shown as the first embodiment on the outlet gas or the gas mixture thus obtained, from the fluid containing HFO-1123 and a C$_{1-5}$ alkane or alkene, impurities other than HFO-1123 can be efficiently removed. The above components other than HFO-1123 contained in the outlet gas or the gas mixture may be removed to a desired extent by a known means such as distillation. Further, the separated FO-1114, FO-1216, CFO-1113 and RC318 are compounds which may form F$_2$C:, and may be recycled as a part of the material composition.

(III) Catalytic Reaction of HFC-134a and Solid Reactant

A material gas containing HFC-134a and a solid reactant are brought into contact with each other in a reactor to allow dehydrofluorination of HFC-134a to proceed, thereby to form a gas containing HFO-1123.

The reaction of HFC-134a and the solid reactant may be represented by the following reaction formula (4) or (5). The reaction formula (4) represents a reaction in a case where the solid reactant functions as a catalyst (Cat.), and the reaction formula (5) represents a reaction in a case where the solid reactant functions as a basic reactant (MOH: M represents a metal).

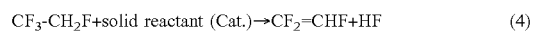

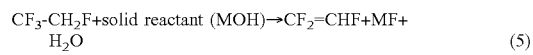

As the solid reactant, calcium oxide, potassium carbonate or the like may be used. Further, the pressure (gauge pressure) in the reactor is preferably from 0 to 5,000 kPa, and the contact time of HFC-134a and the solid reactant in the reactor is preferably from 0.1 to 500 seconds.

For the contact of HFC-134a and the solid reactant, a method may be employed in which a particulate solid reactant having an average particle size of from 1 μm to 5,000 μm is used to form a solid reactant layer, and the solid reactant layer in a fluidized state is brought into contact with and reacted with HFC-134a. In such an embodiment, the temperature at which HFC-134a and the solid reactant are brought into contact with each other is preferably within a range of from 100° C. to 500° C.

In this embodiment, the average particle size is a value measured by a laser diffraction/scattering particle size analyzer.

In the catalytic reaction of HFC-134a and the solid reactant, a reaction product containing HFO-1123 and acidic substances such as hydrogen fluoride is obtained as an outlet gas of the reactor. The acidic substances contained in the outlet gas are removed e.g. by washing with an alkali to obtain a gas mixture. Compounds other than HFO-1123 and the unreacted material component (HFC-134a) contained in the gas mixture may, for example, be hydrogen fluoride, HFO-1132, HFO-1132a, HFC-143, methane, ethane, ethylene, propane, propylene, n-butane, isobutane, 1-n-butene, 2-n-butene, isobutene, HFO-1141, HFO-1252zf, HFO-1243zf, HFO-1234yf, HFO-1234ze, FO-1216, HFC-125, HFC-134, HFC-143a, HFC-227ca, HFC-227ea, HFC-236fa, HFC-236ea, HFC-32, HFC-23 and HFC-41.

By conducting purification shown as the first embodiment on the outlet gas or the gas mixture obtained by the process (III), from the fluid containing HFO-1123 and C$_{1-5}$ alkane or alkene, impurities other than HFO-1123 may be efficiently removed. Further, the above components other than HFO- 1123 contained in the outlet gas or the gas mixture may be removed to a desired extent by a known means such as distillation. Further, HFC-134a separated from the outlet gas or the gas mixture may be recycled as a part of the material gas.

EXAMPLES

Now, the present invention will be described in detail with reference to Examples. However, it should be understood that the present invention is by no means restricted thereto.

Example 1

From a material composition comprising CFO-1113 and hydrogen (hereinafter referred to as a material gas), a gas mixture containing HFO-1123 was obtained as follows.

A reaction tube made of stainless steel having an inner diameter of 23 mm and a length of 50 cm was packed with palladium-supporting activated carbon having 0.5 part by mass of palladium supported on 100 parts by mass of coconut shell activated carbon, to form a catalyst layer having a height of 40 cm. The packing density of the palladium-supporting activated carbon in the catalyst layer was 0.74 g/cm$^3$.

The catalyst layer in the reaction tube thus formed was controlled at 80° C. by an electric heater, and a material composition comprising CFO-1113 and hydrogen (hereinafter sometimes referred to as a material gas) was supplied to the reaction tube under an internal pressure (gauge pressure) of 40 kPa. Hereinafter the pressure means a gauge pressure.

The material gas was made to flow through the reaction tube so that the molar ratio of hydrogen to CFO-1113 (hydrogen/CFO-1113) in the material gas would be 1.0. The contact time of the material gas to the catalyst layer was 30 seconds, and the linear velocity u of the material gas component (CFO-1113) was 1.3 cm/sec.

The maximum temperature of the catalyst layer during the reaction was measured by an insertion thermometer inserted to the catalyst layer while its position was moved. The maximum temperature of the catalyst layer was 236° C.

Here, the outlet gas collected at the outlet of the reactor contained the unreacted material gas in addition to gases formed by the reaction or formed as a by-product.

Then, the outlet gas collected at the outlet of the reactor was washed with an alkali to obtain a gas mixture. The gas mixture was analyzed by gas chromatography (hereinafter referred to as GC) to obtain the molar composition (mol %) of gas components contained in the gas mixture. The molar composition of the gas mixture components thus obtained is taken as "the initial molar composition". Further, the water content in the gas mixture was measured by Karl-Fisher method using CA-100 manufactured by Mitsubishi Chemical Corporation.

Then, a stainless steel tube having an inner diameter of 20 mm and a length of 30 cm was packed with 50 g of particles of synthetic zeolite 3A (manufactured by UNION SHOWA K.K., tradename: Molecular Sieve 3A) to form an adsorption layer, and the gas mixture having the above initial molar composition was made to flow through the adsorption layer at a flow rate of 10 mL/min., and the gas which had passed through the adsorption layer 60 minutes after the start of flow was analyzed by GC to obtain the molar composition (mol %) of the gas after passage.

In order for easy evaluation of adsorptivity of the respective components on molecular sieve 3A, "the initial value" and "the value after passage through MS3A" of the respective components were obtained as follows from "the initial molar composition" and "the molar composition after passage through MS3A". That is, based on the molar composition of HFO-1123 contained in a large amount in the gas mixture, the ratios of the molar composition of each component based on the standard value (mol % of each component/mol % of HFO-1123×100) before and after the passage through the molecular sieve 3A were obtained, and taken as "the initial value" and "the value after passage through MS3A" of each component. The obtained values are shown in Table 1 together with the water content in the gas mixture and in the gas after passage.

Example 2

The reaction was carried out in the same manner as in Example 1, and the outlet gas collected at the outlet of the reactor was washed with an alkali to obtain a gas mixture having "an initial molar composition". The gas mixture was made to flow through the adsorption layer under the same conditions as in Example 1 except that synthetic zeolite 4A (manufactured by UNION SHOWA K.K., tradename: Molecular Sieve 4A) was used, and the molar composition of the gas after passage (hereinafter referred to as "the molar composition after passage through MS4A") was obtained. Further, the water content of the gas after passage was measured in the same manner as the above gas mixture.

Then, "the value after passage through MS4A" which was the ratio based on the molar composition of HFO-1123 was obtained from "the molar composition after passage through MS4A" of each component in the same manner as in Example 1. The obtained values are shown in Table 1 together with the water content in the gas after passage.

Example 3

The reaction was carried out in the same manner as in Example 1, and the outlet gas collected at the outlet of the reactor was washed with an alkali to obtain a gas mixture having "an initial molar composition". The gas mixture was made to flow through the adsorption layer under the same conditions as in Example 1 except that synthetic zeolite 5A (manufactured by UNION SHOWA K.K., tradename: Molecular Sieve 5A) was used, and the molar composition of the gas after passage (hereinafter referred to as "the molar composition after passage through MS5A") was obtained. Further, the water content of the gas after passage was measured in the same manner as the above gas mixture.

Then, "the value after passage through MS5A" which was the ratio based on the molar composition of HFO-1123 was obtained from "the molar composition after passage through MS5A" of each component in the same manner as in Example 1. The obtained values are shown in Table 1 together with the water content in the gas after passage.

TABLE 1

|  |  | Initial value 259 ppm | Example 1 MS3A 2 ppm | Example 2 MS4A 5 ppm | Example 3 MS5A 9 ppm |
|---|---|---|---|---|---|
| Water content | | | | | |
| Ratio of molar composition based on standard value | HFO-1123 | 100.000 | 100.000 | 100.000 | 100.000 |
| | HFO-1132a | 0.401 | 0.387 | 0.321 | n.d. |
| | HFC-152a | 0.054 | 0.053 | 0.028 | n.d. |
| | CFO-1113 | 27.363 | 27.910 | 28.904 | 35.102 |
| | (E)-HFO-1132 | 0.012 | 0.008 | 0.003 | n.d. |
| | (Z)-HFO-1132 | 0.066 | 0.068 | 0.014 | n.d. |
| | HFC-143 | 8.510 | 8.601 | 4.442 | 1.106 |
| | HFC-32 | 0.026 | 0.020 | n.d. | n.d. |
| | HCFO-1122 | 0.082 | 0.092 | 0.068 | 0.010 |
| | (Z)-HCFO-1122a | 0.033 | 0.031 | 0.019 | 0.002 |
| | (E)-HCFO-1122a | 0.041 | 0.046 | 0.021 | 0.005 |
| | HCFC-133b | 1.988 | 1.948 | 1.098 | 0.712 |
| | HFC-152 | 0.069 | 0.067 | 0.035 | n.d. |
| | CFO-1112 | 0.081 | 0.078 | 0.036 | n.d. |
| | HCFC-133 | 0.557 | 0.529 | 0.423 | 0.097 |
| | HCFC-123a | 1.445 | 1.430 | 1.300 | 0.433 |
| | Others | 0.224 | 0.190 | 0.101 | 0.193 |

Further, in Examples 1 to 3, the molar concentrations of HFO-1132(E) and water in the fluid (gas) before and after the contact were calculated based on the molar composition of HFO-1123 in the fluid. From the calculated molar concentrations, the decrease ratios of HFO-1132(E) and water (=(molar concentration before contact−molar concentration after contact)/molar concentration before contact) were calculated. The results are shown in Table 2. In a case where the stainless tube was not packed with the synthetic zeolite and the gas mixture was not brought into contact with the synthetic zeolite, the HFO-1132(E) and water decrease ratios were 0 mol %.

TABLE 2

|  | Example 1 | Example 2 | Example 3 |
|---|---|---|---|
| Synthetic zeolite | MS-3A | MS-4A | MS-5A |
| HFO-1132(E) decrease ratio (%) | 33% | 75% | 100% |
| Water decrease ratio (%) | 99% | 98% | 97% |

It is found from Table 1 that in Example 1 in which molecular sieve 3A was used for purification of the gas fluid obtained in production of HFO-1123, the ratio of the molar composition of the fluid did substantially change as between before and after passage, and only the water content significantly decreased.

Whereas in Example 2 in which molecular sieve 4A was used, although the water content decreased, the ratios of the molar compositions of $C_1$ and $C_2$ saturated compounds to the molar composition of HFO-1123 decreased. Further, in Example 3 in which molecular sieve 5A was used, although the water content decreased, the ratios of the molar compositions of $C_2$ unsaturated compounds other than HFO-1123 to the molar composition of HFO-1123 decreased. Accordingly, it is found that molecular sieve 4A is likely to adsorb $C_1$ and $C_2$ saturated compounds, and molecular sieve 5A is likely to adsorb, in addition to $C_1$ and $C_2$ saturated compounds, $C_2$ saturated compounds other than HFO-1123.

From such results in Examples, it is found that molecular sieve 3A which is synthetic zeolite 3A is optimum to remove, from a fluid containing HFO-1123, only water without removal of organic components such as a $C_{1-5}$ alkane or alkene.

Further, it is found from Table 2 that in Examples 1 to 3 in which molecular sieve 3A, 4A or 5A was used, HFO-1132(E) is likely to be adsorbed. Accordingly, by bringing the fluid in the present invention into contact with at least one member selected from molecular sieves 3A, 4A and 5A, the $C_{1-5}$ alkane or alkene, particularly HFO-1132(E) having a boiling point close to that of HFO-1123, can be efficiently removed. Particularly, in order to remove HFO-1132(E) efficiently, use of molecular sieve 4A which is synthetic zeolite 4A is more preferred, and molecular sieve 5A which is synthetic zeolite 5A is optimum.

INDUSTRIAL APPLICABILITY

According to the purification method of the present invention, from a fluid containing HFO-1123 and a $C_{1-5}$ alkane or alkene, impurities other than HFO-1123, such as the $C_{1-5}$ alkane or alkene or water may be efficiently removed.

Further, according to the production method of the present invention, by purifying the fluid containing HFO-1123, from the fluid containing HFO-1123 and a $C_{1-5}$ alkane or alkene, impurities other than HFO-1123, such as the $C_{1-5}$ alkane or alkene or water may be efficiently removed.

This application is a continuation of PCT Application No. PCT/JP2015/054643 filed on Feb. 19, 2015, which is based upon and claims the benefit of priorities from Japanese Patent Application No. 2014-030854 filed on Feb. 20, 2014 and Japanese Patent Application No. 2014-092296 filed on Apr. 28, 2014. The contents of those applications are incorporated herein by reference in their entireties.

What is claimed is:

1. A method for producing trifluoroethylene, the method comprising:
   bringing a fluid comprising trifluoroethylene and (E)-1,2-difluoroethylene into contact with at least one synthetic zeolite selected from the group consisting of synthetic zeolites 4A and 5A such that (E)-1,2-difluoroethylene is adsorbed in the at least one synthetic zeolite.

2. The method according to claim 1, further comprising:
   reducing chlorotrifluoroethylene with hydrogen gas in the presence of a catalyst to produce the fluid before the fluid is brought into contact with the at least one synthetic zeolite.

3. The method according to claim 1, further comprising:
   subjecting a composition comprising chlorodifluoromethane and/or tetrafluoroethylene and chlorofluoromethane to a synthetic reaction involving heat decomposition in the presence of a heating fluid to produce the fluid before the fluid is brought into contact with the at least one synthetic zeolite.

4. The method according to claim 1, further comprising:
subjecting 1,1,1,2-tetrafluoroethane to dehydrofluorination in the presence of an alkali metal and/or an alkaline earth metal to produce the fluid before the fluid is brought into contact with the at least one synthetic zeolite.

5. The method according to claim 1, wherein the synthetic zeolite is subjected to a heat treatment by a dry gas of from 100 to 400° C. or subjected to a heat treatment under reduced pressure before the fluid is brought into contact with the at least one synthetic zeolite.

6. A method for producing trifluoroethylene, the method comprising:
bringing a fluid comprising trifluoroethylene, (E)-1,2-difluoroethylene and water, into contact with synthetic zeolites 3A such that (E)-1,2-difluoroethylene and water are adsorbed in the synthetic zeolite 3A.

7. The method according to claim 6, further comprising:
reducing chlorotrifluoroethylene with hydrogen gas in the presence of a catalyst to produce the fluid before the fluid is brought into contact with the synthetic zeolite 3A.

8. The method according to claim 6, further comprising:
subjecting a composition comprising chlorodifluoromethane and/or tetrafluoroethylene and chlorofluoromethane to a synthetic reaction involving heat decomposition in the presence of a heating fluid to produce the fluid before the fluid is brought into contact with the synthetic zeolite 3A.

9. The method according to claim 6, further comprising:
subjecting 1,1,1,2-tetrafluoroethane to dehydrofluorination in the presence of an alkali metal and/or an alkaline earth metal to produce the fluid before the fluid is brought into contact with the synthetic zeolite 3A.

10. The method according to claim 6, wherein the synthetic zeolite is subjected to a heat treatment by a dry gas of from 100 to 400° C. or subjected to a heat treatment under reduced pressure before the fluid is brought into contact with the synthetic zeolite 3A.

* * * * *